US012599648B2

(12) United States Patent
Ocvirk

(10) Patent No.: US 12,599,648 B2
(45) Date of Patent: Apr. 14, 2026

(54) PHARMACEUTICAL COMPOSITION COMPRISING A COMBINATION OF A GUANYLATE CYCLASE C (GUCY2C) AGONIST AND A SHORT-CHAIN FATTY ACID OR PRODRUG THEREOF

(71) Applicant: Sören Ocvirk, Kranzberg (DE)

(72) Inventor: Sören Ocvirk, Kranzberg (DE)

( * ) Notice: Subject to any disclaimer, the term of this patent is extended or adjusted under 35 U.S.C. 154(b) by 669 days.

(21) Appl. No.: 18/011,718

(22) PCT Filed: Jun. 30, 2020

(86) PCT No.: PCT/EP2020/068394
§ 371 (c)(1),
(2) Date: Dec. 20, 2022

(87) PCT Pub. No.: WO2022/002369
PCT Pub. Date: Jan. 6, 2022

(65) Prior Publication Data
US 2023/0226143 A1 Jul. 20, 2023

(51) Int. Cl.

| | |
|---|---|
| ***A61K 38/12*** | (2006.01) |
| ***A61K 31/19*** | (2006.01) |
| ***A61K 38/16*** | (2006.01) |
| ***A61K 45/06*** | (2006.01) |
| ***A61P 1/00*** | (2006.01) |
| ***A61P 35/00*** | (2006.01) |

(52) U.S. Cl.
CPC .............. *A61K 38/12* (2013.01); *A61K 31/19* (2013.01); *A61K 38/164* (2013.01); *A61K 45/06* (2013.01); *A61P 1/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 2015/0094272 A1 | 4/2015 | Kessler et al. | |
| 2017/0000741 A1* | 1/2017 | Betz | B65B 7/28 |
| 2019/0350863 A1* | 11/2019 | Hashash | A61K 9/2027 |
| 2022/0008533 A1* | 1/2022 | Shailubhai | A61K 38/08 |
| 2022/0202881 A1* | 6/2022 | Dorrestein | A61P 35/00 |
| 2022/0257690 A1 | 8/2022 | Czap | |
| 2023/0096663 A1* | 3/2023 | Judkins | A61K 31/422<br>514/214.03 |

FOREIGN PATENT DOCUMENTS

| | | | |
|---|---|---|---|
| CN | 110935007 | 3/2020 | A61K 38/10 |
| JP | 2014-524444 A2 | 9/2014 | |
| JP | 2017-537960 A2 | 12/2017 | |
| JP | 2018-519252 A2 | 7/2018 | |
| JP | 2019-509278 A2 | 4/2019 | |
| JP | 2019-512019 A2 | 5/2019 | |
| WO | 2010019266 | 2/2010 | A61K 38/10 |
| WO | 2013025969 | 2/2013 | A61K 38/10 |
| WO | 2014197720 | 12/2014 | C07K 14/81 |
| WO | WO2016097933 A1 | 6/2016 | |
| WO | WO2016174616 A1 | 11/2016 | |
| WO | WO2017145031 A1 | 8/2017 | |
| WO | WO2020089396 A2 | 5/2020 | |

OTHER PUBLICATIONS

International Preliminary Report on Patentability issued in PCT/EP2020/068394, dated Oct. 4, 2020, 15 pages.

International Search Report and Written Opinion issued in PCT/EP2020/068394, dated Feb. 26, 2021, 14 pages.

Andresen et al., "Linaclotide Acetate. Guanylate cyclase C receptor agonist, treatment of irritable bowel syndrome, treatment of constipation" *Drugs of the Future* Jul. 2008, 33: 7; 570-576, Abstract only, 3 pages.

Donohoe et al. "A Gnotobiotic Mouse Model Demonstrates That Dietary Fiber Protects against Colorectal Tumorigensis in a Microbiota- and Butyrate-Dependent Manner" *Cancer Discovery* Dec. 2014, 1387-1397, 11 pages.

Hoevenaars et al. "BIOCLAIMS standard diet (BIOsd): a reference diet for nutritional physiology" *Genes Nutr.* (2012) 7:399-404, 6 pages.

Islam et al. "Clinical utility of plecanatide in the treatment of chronic idiopathic constipation" *International Journal of General Medicine* 2018:11 323-330, 8 pages.

O'Keefe et al., "Diet, microorganisms and their metabolites, and colon cancer" *Nature Reviews Gastroenterology & Hepatology* 13, 691-706 (2016), Abstract only, 2 pages.

Reynolds et al., "Carbohydrate quality and human health: a series of systematic reviews and meta-analyses" *Lancet* 2019: 393: 434-45, 12 pages.

Sharman et al., "Cyclic-GMP-Elevating Agents Suppress Polyposis in Apc$^{Min}$ Mice by Targeting the Preneoplastic Epithelium" *Cancer Prevention Research* 2018, 81-92, 12 pages.

VanDussen et al., "Development of an enhanced human gastrointestinal epithelial culture system to facilitate patient-based assays" *Gut* 2015; 64:911-920, 10 pages.

(Continued)

*Primary Examiner* — Daniel C Gamett
(74) *Attorney, Agent, or Firm* — HAYES SOLOWAY P.C.

(57) ABSTRACT

A pharmaceutical composition includes a combination of a guanylate cyclase C (GUCY2C) agonist and a short-chain C2 to C5 fatty acid and/or a salt and/or a prodrug thereof in a therapeutically effective amount and one or more pharmaceutically acceptable excipients as well as to a method of preventing and/or treating colorectal tumorigenesis and/or carcinogenesis and/or chronic intestinal inflammation and/or cystic fibrosis related gastrointestinal manifestations by administering to a patient, who has developed or is at risk to develop colorectal tumorigenesis and/or carcinogenesis and/or chronic intestinal inflammation and/or cystic fibrosis related gastrointestinal manifestations, a therapeutically effective amount of a combination of a GUCY2C agonist and a short-chain C2 to C5 fatty acid or a salt or a prodrug thereof.

16 Claims, 9 Drawing Sheets

(56) References Cited

OTHER PUBLICATIONS

Weinberg et al., "Bioactivity of Oral Linaclotide in Human Colorectum for Cancer Chemoprevention" *Cancer Prevention Research* Jun. 2017, 10(6) 345-353, 10 pages.

"Journal of Pediatric Gastroenterology and Nutrition", vol. 75, Suppiement 1, Oct. 2022, Abstract No. 617, pp. S449-S450, 3 pgs.

* cited by examiner

PHARMACEUTICAL COMPOSITION COMPRISING A COMBINATION OF A GUANYLATE CYCLASE C (GUCY2C) AGONIST AND A SHORT-CHAIN FATTY ACID OR PRODRUG THEREOF

TECHNICAL FIELD

The present invention relates to a pharmaceutical composition comprising a combination of a guanylate cyclase C (GUCY2C) agonist and a short-chain C2 to C5 fatty acid and/or a salt and/or a prodrug thereof in a therapeutically effective amount and one or more pharmaceutically acceptable excipients as well as to a method of preventing and/or treating colorectal tumorigenesis and/or carcinogenesis and/or chronic intestinal inflammation and/or cystic fibrosis related gastrointestinal manifestations by administering to a patient, who has developed or is at risk to develop colorectal tumorigenesis and/or carcinogenesis and/or chronic intestinal inflammation and/or cystic fibrosis related gastrointestinal manifestations, a therapeutically effective amount of a combination of a GUCY2C agonist and a short-chain C2 to C5 fatty acid or a salt or a prodrug thereof.

BACKGROUND ART

Colorectal cancer (CRC) is the fourth leading cause of cancer deaths worldwide and shows rising incidence in most countries. The majority of sporadic CRC cases results from accumulated genetic alterations in response to detrimental environmental factors, in particular diet. The convincing contribution of diet to CRC risk and the numerous unsolved challenges in anti-cancer therapy (e.g., patients responding differently to chemotherapy, surgery being the only available method to cure CRC patients) emphasize the need for early and targeted prevention of CRC in high-risk groups that are characterized by a detrimental dietary pattern, for example.

Dietary fiber is comprised of a heterogeneous group of complex carbohydrates that are indigestible for the host and fermented under anaerobic conditions by specific gut bacteria in the colonic lumen to short-chain fatty acids (SCFA), such as acetate, propionate and butyrate. Several clinical and experimental studies provided convincing evidence for fiber reducing CRC risk (O'Keefe S J D. Diet, microorganisms and their metabolites, and colon cancer. Nat Rev Gastroenterol Hepatol. 2016; 13:691-706): for example, a recent meta-analysis covering 185 prospective trials and 58 clinical studies provided evidence for an inverse correlation of fiber intake and CRC risk (Reynolds A, Mann J, Cummings J, Winter N, Mete E, Morenga L T . Carbohydrate quality and human health: a series of systematic reviews and meta-analyses. The Lancet. 2019;0). Focusing on the observational studies in the meta-analysis, the highest fiber consumption was associated with a significant decrease in CRC incidence compared to lowest intake (cf. Reynolds et al. ibid.). Since a linear dose-response relationship for dietary fiber and CRC incidence was identified, the authors suggested the adult daily intake of fiber to be not less than 25-29 g and speculated that higher amounts would have greater protective effects (cf. Reynolds et al. ibid).

The fiber-derived SCFA butyrate is the main source of energy for colonic epithelial cells (colonocytes), a major regulator of colonocyte proliferation and differentiation, and has potent tumorsuppressive effects in the colon (cf. O'Keefe ibid.). Butyrate (or butyric acid, respectively) is a short-chain monocarboxylic fatty acid and belongs to the volatile fatty acids (together with acetic acid and propionic acid). There are two isomers (n-butyric acid, iso-butyric acid), of which n-butyric acid is found in high concentrations in the colonic lumen of humans (and rodent models).

At ambient temperature, n-butyric acid is in liquid form and has a characteristic rancid butter odor, which is noticed by humans and by many animal species even in very low concentrations. Under laboratory conditions and in experimental trials, either the sodium salt of butyric acid or fiber-supplemented diets are used to reach/mimic high levels of butyrate. Due to efficient absorption of butyrate in the gut, oral administration of sodium butyrate is less likely to promote high butyrate concentrations in the colon. Being the "natural way" of supplying colonic epithelial cells with butyrate, fiber supplementation may be effective to provide butyrate, but results in divergent effects due to different types of fiber and differences in gut microbiota composition (e.g., high or low numbers of butyrate-producing bacteria).

The prodrug tributyrin releases high amounts of butyrate in distal parts of the colon. Tributyrin may be advantageous over butyric acid in that it does not have an unpleasant odor or taste and demonstrated more potent effects in suppressing intestinal tumorigenesis and chronic intestinal inflammation than sodium butyrate, the sodium salt of butyric acid. Tributyrin was initially synthesized during the 1920ies and is commercially available through chemical distributors. Tributyrin is an ester of butyric acid, i.e. an ester composed of butyric acid and glycerol with the IUPAC name 1,3-di(butanoyloxy)propan-2-yl butanoate. Tributyrin is a lipophilic compound which is only poorly soluble in water.

In an experimental study, Donohoe et al. associated germ-free wild-type mice with a defined mix of gut bacteria with or without the butyrate-producing bacterium *Butyvibrio fibrisolvens*, kept mice on a low- or high-fiber diet and induced colorectal tumorigenesis using azoxymethane (AOM) and dextran sodium sulfate (DSS) (Donohoe D R, Holley D, Collins L B, Montgomery S A, Whitmore A C, Hillhouse A, Curry K P, Renner S W, Greenwalt A, Ryan E P, et al. A gnotobiotic mouse model demonstrates that dietary fiber protects against colorectal tumorigenesis in a microbiota- and butyrate-dependent manner. Cancer Discov. 2014; 4:1387-97). Mice receiving a high-fiber diet and colonized with *B. fibrisolvens* showed significantly fewer colonic tumors after treatment with azoxymethane (AOM) and dextran sodium sulfate (DSS) compared to mice on a high-fiber diet without *B. fibrisolvens*. The protective effect of *B. fibrisolvens* colonization was abolished when mice received a low-fiber diet (cf. Donohoe et al. ibid.). This was confirmed by a second experiment where wild-type *B. fibrisolvens* protected from colonic tumor formation in a fiber-dependent manner compared to an isogenic deletion mutant that produced less butyrate (cf. Donohoe et al. ibid.). Critically, an additional group of mice that received a diet supplemented with tributyrin, the stable prodrug of butyrate that shows delayed absorption in the gut, had the lowest tumor levels in the colon after AOM/DSS treatment (cf. Donohoe et al. ibid.).

Guanylate cyclase C (GUCY2C) is a member of the transmembrane guanylate cyclase receptors and is expressed on the apical side of intestinal epithelial cells throughout the whole intestine. Originally, GUCY2C was identified as orphan receptor for the bacterial heat-stable enterotoxin STa produced by enterotoxigenic *Escherichia coli*. The binding of STa toxin to GUCY2C mediates excessive secretion of fluids into the intestinal lumen resulting in massive diarrhea, clinically also known as "traveler's diarrhea". At cellular level, agonists of GUCY2C trigger the intracellular conversion of guanosine triphosphate (GTP) to cyclic guanosine monophosphate (cGMP), which activates the cystic fibrosis conductance regulator (CFTR) and inhibits the sodium-hydrogen-exchanger 3 (NHE3). This mediates an increased chloride secretion into and an impaired sodium ion uptake from the intestinal lumen and leads to an osmotic gradient that promotes the accumulation of fluids in the gut lumen.

In addition to STa toxin, two intestinal hormones were identified as ligands for GUCY2C: guanylin and uroguanylin. These endogenous peptides are produced by intestinal epithelial cells and induce GUCY2C signaling in an autocrine or paracrine manner. Compared to STa toxin, guanylin (encoded by GUCA2A) and uroguanylin (encoded by GUCA2B) have a lower affinity to GUCY2C and a higher susceptibility to proteolytic degradation in the gut lumen. Although dominant in different segments in the intestine (guanylin in colon, uroguanylin in small intestine), both intestinal peptide hormones are potent inducers of GUCY2C signaling in colonocytes, which regulates cellular functions beyond electrolyte management.

The GUCY2C signaling axis recently emerged as a major driver of intestinal epithelial cell functions such as proliferation and differentiation, organization of the crypt-villus axis, barrier integrity and DNA-repair mechanisms. Silencing of GUCY2C signaling results in significant colonocyte dysfunction, which is implicated in the pathogenesis of sporadic CRC. The tumorsuppressive function of GUCY2C signaling is supported by the observation that the expression of its ligand guanylin is lost in intestinal tumorigenesis as well as in human colon carcinoma cells and characterizes early stages of intestinal neoplastic transformation. Several studies provide experimental evidence for a tumorsuppressive function of GUCY2C signaling. Consistently, the expression of guanylin is lost in colonic tumors, but is still present in the adjacent healthy mucosa, suggesting a high potential for restored guanylin expression in the suppression of intestinal tumorigenesis. The stimulation of GUCY2C signaling by administration of its ligands inhibited adenomatous polyp formation in a CRC mouse model and suppressed proliferation in human colon carcinoma cells. Its fundamental role in the homeostasis of intestinal epithelial cells is highlighted by the fact that GUCY2C signaling is also down-regulated in the inflamed mucosa of IBD patients and during chronic colitis in rats.

Due to the extensive effects on colonocytes, the GUCY2C signaling axis has raised considerable interest regarding potential therapeutic applications. Analogs of guanylin, uroguanylin or the STa toxin were designed and tested for potential application in gastrointestinal disorders. Taking advantage of its role in intestinal electrolyte management, the guanylin analog linaclotide (brand names Constella, Linzess) was approved as GUCY2C agonist to treat chronic constipation and improve gastrointestinal transit and visceral hypersensitivity in irritable bowel syndrome (IBS). More than 10% of people taking linaclotide have diarrhea. Between 1% and 10% of people have decreased appetite, dehydration, low potassium, dizziness when standing up too quickly, nausea, vomiting, urgent need to defecate, fecal incontinence, and bleeding in their colon, rectum, and anus. The US label of commercialized linaclotide drugs comprises a warning of to not use linaclotide in children less than 6 years old and to avoid in people from 6 to 18 years old, due to the risk of serious dehydration.

Pleacanatide (brand name Trulance) is an agonist of GUCY2C. The main side effect is the risk of serious dehydration, that is why children less than 6 years old and people from 6 to 18 years old should not receive the drug.

Dolcanatide (CAS Number: 1092457-65-2) is an orally administered analog of the human endogenous natriuretic hormone uroguanylin and a GUCY2C agonist, with potential laxative, anti-nociceptive and anti-inflammatory activities. Upon administration, dolcanatide, by mimicking uroguanylin, binds to and activates GUCY2C locally on endothelial cells in the gastrointestinal (GI) tract, without entering the systemic circulation. The main side effect is the risk of serious dehydration.

In view of the prior art there still exists a need for improving prevention and/or treatment of colorectal tumorigenesis and/or carcinogenesis and/or chronic intestinal inflammation and/or cystic fibrosis related gastrointestinal manifestations, and/or reducing side effects of existing prophylaxes and/or reducing side effects of existing therapies.

Thus, the problem addressed by the present invention is to provide a pharmaceutical composition with improved effect in preventing and/or treating colorectal tumorigenesis and/or carcinogenesis and/or chronic intestinal inflammation and/or cystic fibrosis related gastrointestinal manifestations in a patient, who has or is at risk to develop colorectal tumorigenesis and/or carcinogenesis and/or chronic intestinal inflammation and/or cystic fibrosis related gastrointestinal manifestations, and/or reducing side effects of existing prophylaxes or therapies.

BRIEF DESCRIPTION OF THE INVENTION

The aforementioned aim is solved at least in part by means of the claimed inventive subject matter. Advantages (preferred embodiments) are set out in the detailed description hereinafter and/or the accompanying figures as well as in the dependent claims.

Accordingly, a first aspect of the invention relates to a pharmaceutical composition comprising a combination of a guanylate cyclase C (GUCY2C) agonist and a short-chain C2 to C5 fatty acid or a salt or a prodrug thereof in a therapeutically effective amount and one or more pharmaceutically acceptable excipients.

A second aspect of the invention relates to a method of preventing and/or treating colorectal tumorigenesis and/or carcinogenesis and/or chronic intestinal inflammation and/or cystic fibrosis related gastrointestinal manifestations, by administering to a patient, who has developed or is at risk to develop colorectal tumorigenesis and/or carcinogenesis and/or chronic intestinal inflammation and/or cystic fibrosis related gastrointestinal manifestations, a therapeutically effective amount of a combination of a GUCY2C agonist and a short-chain C2 to C5 fatty acid or a salt or a prodrug thereof.

The inventive aspects of the present invention as disclosed hereinbefore can comprise any possible (sub-)combination of the preferred inventive embodiments thereof as set out in the dependent claims or as disclosed in the following detailed description and/or in the accompanying figures, provided the resulting combination of features is reasonable to a person skilled in the art.

BRIEF DESCRIPTION OF THE DRAWINGS

Further characteristics and advantages of the present invention will ensue from the accompanying drawings, wherein.

DETAILED DESCRIPTION OF THE INVENTION

Figure 1:
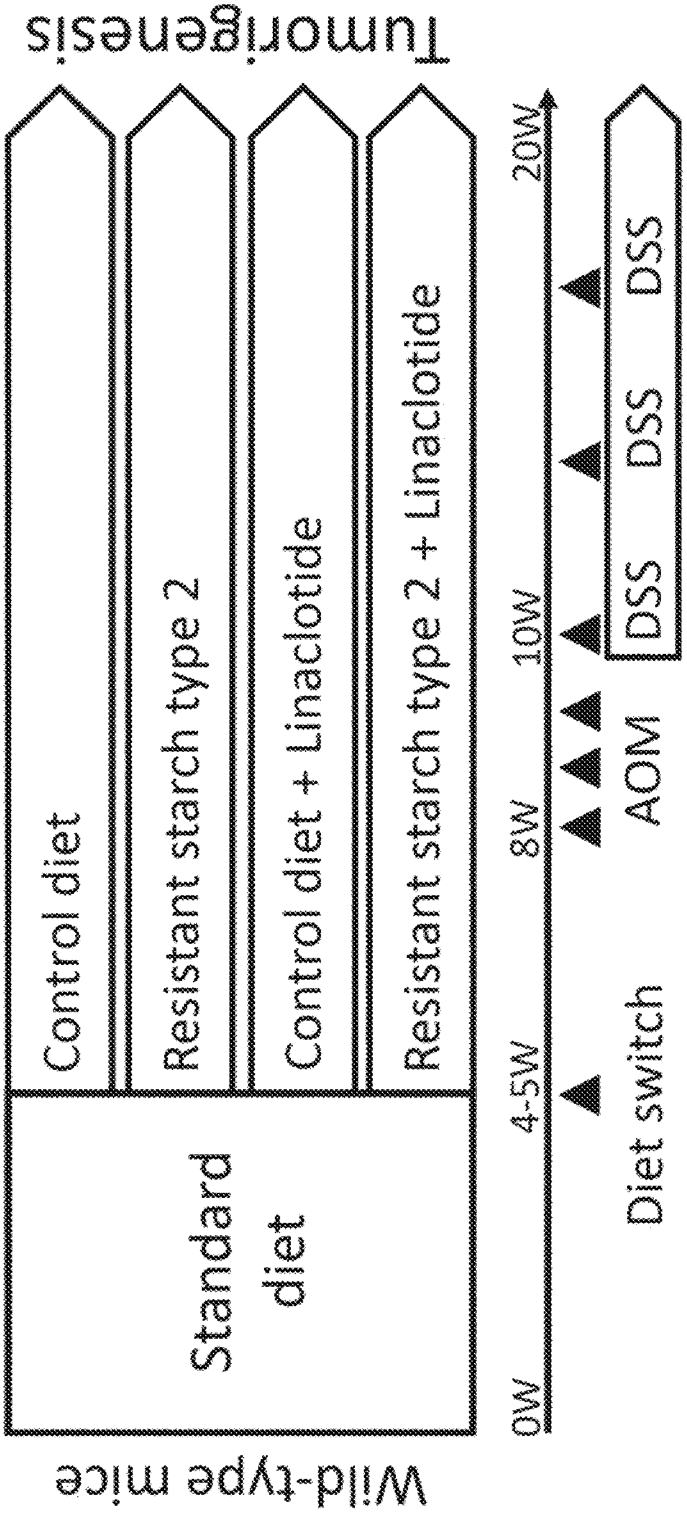
FIG. 1 represents a schematic study layout of a mouse trial using an AOM/DSS-based CRC mouse model.

As set out in more detail hereinafter, the inventor of the different inventive aspects has found out that the combined use of a guanylate cyclase C (GUCY2C) agonist and a short-chain C2 to C5 fatty acid and/or a salt and/or a prodrug thereof in a therapeutically effective amount exhibits a synergistic effect on the prevention and/or treatment of colorectal tumorigenesis and/or carcinogenesis and/or chronic intestinal inflammation and/or cystic fibrosis related gastrointestinal manifestations in a patient, who has or is at risk to develop colorectal tumorigenesis and/or carcinogenesis and/or chronic intestinal inflammation and/or cystic fibrosis related gastrointestinal manifestations. This synergistic effect is shown in the Example section under Results and Discussion item 1 and FIGS. 2*a*) to 2*d*).

Furthermore, the short-chain C2 to C5 fatty acid or a salt or a prodrug thereof reduces one or more undesired side effects of guanylate cyclase C (GUCY2C) agonists, such as diarrhea and thus reducing the risk of severe dehydration of a patient. Accordingly, the inventive pharmaceutical composition or the inventive treatment is also suitable for patients, such as children, which otherwise could not be treated with the GUCY2C agonists. This effect is shown in Example section under Results and Discussion item 1 and FIGS. 4*a*) to 4*b*).

In context of the present invention, the term "patient" refers to a human or an animal, preferably a human, who has already developed colorectal tumorigenesis and/or carcinogenesis and/or chronic intestinal inflammation and/or cystic fibrosis related gastrointestinal manifestations or is at a certain risk to develop colorectal tumorigenesis and/or carcinogenesis and/or chronic intestinal inflammation and/or cystic fibrosis related gastrointestinal manifestations.

In the context of the present invention, the term "disease" refers to colorectal tumorigenesis and/or carcinogenesis and/or chronic intestinal inflammation and/or cystic fibrosis related gastrointestinal manifestations, wherein colorectal tumorigenesis and/or carcinogenesis is preferably selected from the group consisting of colorectal cancer (CRC) including early stages preceding CRC, such as crypt dysplasia, crypt hyperplasia, colorectal adenoma, colorectal adenomatous polyps, or colorectal carcinoma; or wherein chronic intestinal inflammation is preferably selected from inflammatory bowel diseases (IBD) including Crohn's disease, or ulcerative colitis; or wherein cystic fibrosis related gastrointestinal manifestations preferably includes intestinal mucus inspissation, intestinal dysmotility, or distal intestinal obstruction syndrome.

In the context of the present invention, the term "a guanylate cyclase C (GUCY2C) agonist" refers to one or more guanylate cyclase C (GUCY2C) agonists.

In the context of the present invention, the term "a short-chain C2 to C5 fatty acid and/or a salt and/or a prodrug thereof" refers to one or more short-chain C2 to C5 fatty acids and/or a salts and/or a prodrugs thereof.

As already mentioned above, the first inventive aspect relates to a pharmaceutical composition comprising a combination of a guanylate cyclase C (GUCY2C) agonist and a short-chain C2 to C5 fatty acid and/or a salt and/or a prodrug thereof in a therapeutically effective amount and one or more pharmaceutically acceptable excipients.

According to the present invention, the composition may comprise one or more GUCY2C agonists.

According to one embodiment of the present invention any suitable GUCY2C agonist, in particular orally administrable GUCY2C agonist may be used in the context of the different inventive aspects. According to one embodiment, the one or more GUCY2C agonists are selected from the group consisting of linaclotide, plecanatide, dolcanatide and heat-stable enterotoxin STa (STa toxin).

Linaclotide (CAS Number: 851199-59-2) exhibits the following chemical formula:

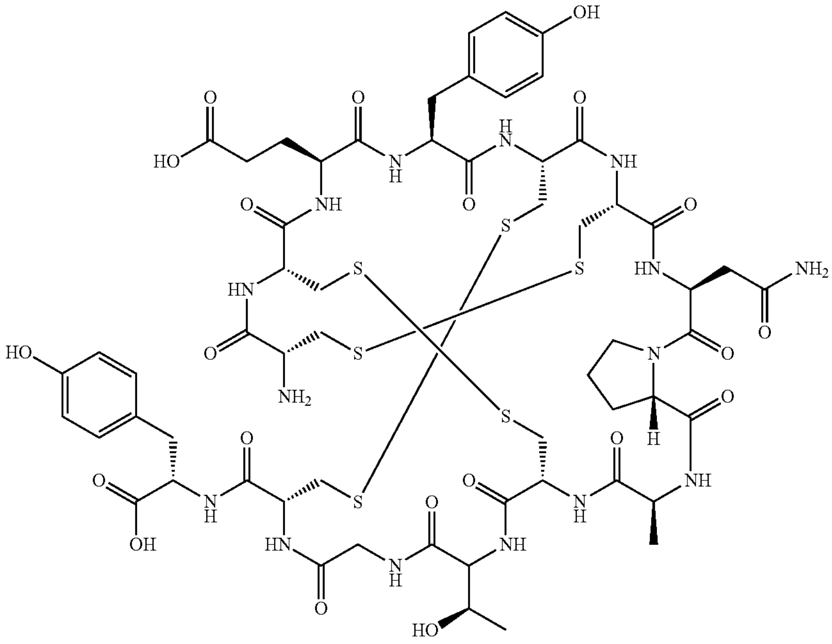 [SMILES: C[C@@H]1NC(=O)[C@@H]2CCCN2C(=O)[C@H](CC(N)=O)NC(=O)[C@@H]2CSSC[C@H](N)C(=O)N[C@H]3CSSC[C@H](NC1=O)C(=O)NC([C@@H](C)O)C(=O)NCC(=O)N[C@H](C(=O)N[C@@H](Cc1ccc(O)cc1)C(=O)O)CSSC[C@H](NC(=O)[C@H](Cc1ccc(O)cc1)NC(=O)[C@H](CCC(=O)O)NC3=O)C(=O)N2]

Linaclotide is a tetradecapeptide mimic of endogenous guanylin and uroguanylin. In order to avoid degradation when orally administering linaclotide, linaclotide, preferably exhibits according to the present invention a suitable formulation for reducing degradation, preferably exhibiting a suitable enteric coating.

Pleacanatide (CAS Number: 467426-54-6) represents a polypeptide comprising 16 amino acids being structurally close to uroguanylin and only exhibiting a substitution of aspartic acid (Asp) in position 3 by glutamic acid (Glu). As with most orally ingested peptides, plecanatide is degraded by intestinal enzymes. Accordingly, plecanatide, when being orally administered, preferably exhibits according to the present invention a suitable formulation for reducing degradation, preferably exhibiting a suitable enteric coating.

Dolcanatide (CAS Number: 1092457-65-2) is an analog of the human endogenous natriuretic hormone uroguanylin and a GUCY2C agonist. As with most orally ingested peptides, dolcanatide is degraded by intestinal enzymes. Accordingly, dolcanatide, when being orally administered, preferably exhibits according to the present invention a suitable formulation for reducing degradation, preferably exhibiting a suitable enteric coating.

Heat-stable entertoxine STa (STa toxin) is a guanylate cyclase C (GUCY2C) agonist is a secretory peptide produced by bacterial strains, such as enterotoxigenic *Escherichia coli* exhibiting a 19-residue peptide containing three disulphide bridges that are functionally important. STa contains an N-terminal signal peptide composed of two domains, Pre and Pro, involved in extracellular toxin release, and a core enterotoxigenic domain. The binding of STa toxin to GUCY2C mediates excessive secretion of fluids into the intestinal lumen resulting in massive diarrhea, clinically also known as "traveler's diarrhea". At cellular level, agonists of GUCY2C trigger the intracellular conversion of guanosine triphosphate (GTP) to cyclic guanosine monophosphate (cGMP), which activates the cystic fibrosis conductance regulator (CFTR) and inhibits the sodium-hydrogen-exchanger 3 (NHE3). This mediates an increased chloride secretion into and an impaired sodium ion uptake from the intestinal lumen and leads to an osmotic gradient that promotes the accumulation of fluids in the gut lumen.

According to one embodiment of the inventive pharmaceutical composition, the composition comprises the GUCY2C agonist, e.g. linaclotide, plecanatide, dolcanatide or STa toxin, in an amount of 0.1 to 1,000 mg per dose unit.

According to the present invention, the inventive composition may comprise one or more short-chain C2 to C5 fatty acids and/or salts and/or prodrugs thereof. Prodrugs of a SCFA are compounds that release under physiological conditions the respective SCFA or salt thereof. As an example, an ester of a SCFA is according to the present invention regarded as a prodrug, as it releases under physiological conditions the SCFA or a salt thereof.

According to an embodiment of the present invention, the one or more short-chain C2 to C5 fatty acids (SCFA) and/or salts and/or prodrugs thereof is/are selected from the group consisting of acetic acid, acetate, acetic acid ester, propionic acid, propionate, propionic acid ester, butyric acid, butyrate, e.g. sodium butyrate, butyric acid ester, e.g. tributyrin, valeric acid, valerate, and valeric acid ester.

Butyric acid, butyrate, preferably sodium butyrate, and/or tributyrin may be preferred in view of their potency of inhibiting epithelia inflammatory response or epithelial transformation. Within this group, tributyrin may be advantageous over butyric acid in that it does not have an unpleasant odor or taste and is contemplated to be an even more potent inhibitor of epithelia inflammatory response than sodium butyrate, the sodium salt of butyric acid. Some studies show that tributyrin is a more effective and better tolerated anti-inflammatory agent in the treatment of chronic inflammatory bowel diseases. Tributyrin was initially synthesized during the 1920ies. It is commercially available through a number of chemical distributors. Tributyrin is an ester of butyric acid, i.e. an ester composed of butyric acid and glycerol with the IUPAC name 1,3-di(butanoyloxy) propan-2-yl butanoate. Tributyrin is a lipophilic compound which is only poorly soluble in water.

According to one embodiment of the inventive pharmaceutical composition, the composition comprises the short-chain C2 to C5 fatty acid and/or salt and/or prodrug, e.g. butyric acid or butyrate or tributyrin in an amount of 0.1 to 5,000 mg per dose unit.

According to the present invention, the one or more of the GUCY2C agonists, e.g., linaclotide, plecanatide, dolcanatide and/or STa toxin may be combined with one or more of the SCFA or salts or prodrugs thereof selected from the group consisting of acetic acid, acetate, acetic acid ester, propionic acid, propionate, propionic acid ester, butyric acid, butyrate, e.g. sodium butyrate, butyric acid ester, e.g. tributyrin, valeric acid, valerate, and valeric acid ester. According to one embodiment of the present invention, linaclotide, plecanatide, dolcanatide and/or STa is/are combined with butyric acid, butyrate, e.g. sodium butyrate, and/or butyric acid ester, e.g. tributyrin, preferably linaclotide is combined with butyric acid, butyrate, e.g. sodium butyrate, and/or butyric acid ester, e.g. tributyrin.

Another embodiment of the present invention relates to the inventive pharmaceutical composition, wherein the pharmaceutical composition comprises in addition to a GUCY2C and a short-chain C2 to C5 fatty acid and/or salt and/or prodrug thereof one or more farnesoid X receptor (FXR) agonists, preferably including one or more bile acids and/or one or more bile acid derivatives, more preferably wherein the one or more farnesoid X receptor (FXR) agonists are selected from the group consisting of chenodeoxycholic acid (IUPAC: (R)-((3R,5S,7R,8R,9S,10S,13R,14S,17R)-3,7-dihydroxy-10,13-dimethylhexadecahydro-1H-cyclopenta[a]phenanthren-17-yl)pentanoic acid), cholic acid (IUPAC: R)-4-((3R,5S,7R,8R,9S,10S,12S,13R,14S,17R)-3,7,12-Trihydroxy-10,13-dimethylhexadecahydro-1H-cyclopenta[a]phenanthren-17-yl)pentanoic acid), deoxycholic acid (IUPAC: (3α,5β,12α,20R)-3,12-Dihydroxycholan-24-oic acid), lithocholic acid (IUPAC: (4R)-4-[(3R,5R,8R,9S,10S,13R,14S,17R)-3-Hydroxy-10,13-dimethyl-2,3,4,5,6,7,8,9,11,12,14,15,16,17-tetradecahydro-1H-cyclopenta[a]phenanthren-17-yl]pentanoic acid), taurocholic acid (IUPAC: 2-{[(3α,5β,7α,12α)-3,7,12-trihydroxy-24-oxocholan-24-yl]amino}ethanesulfonic acid), ursodeoxycholic acid (IUPAC: (R)-4-((3R,5S,7S,8R,9S,10S,13R,14S,17R)-3,7-dihydroxy-10,13-dimethylhexadecahydro-1H-cyclopenta[a]phenanthren-17-yl)pentanoic acid), semi-synthetic obeticholic acid (IUPAC: 6α-ethyl-chenodeoxycholic acid), synthetic GW 4064 (IUPAC: 3-[2-[2-Chloro-4-[[3-(2,6-dichlorophenyl)-5-(1-methylethyl)-4-isoxazolyl]methoxy]phenyl]ethenyl]benzoic acid).

Farnesoid X receptor (FXR) is a nuclear receptor expressed in the intestinal epithelium, which is activated/inhibited by bile acids and bile acid derivatives as its ligands. As a nuclear receptor, FXR is involved in regulation of gene expression and the genes encoding for guanylin (GUCA2A) and uroguanylin (GUCA2B) may be potential targets for FXR in the intestinal epithelium. Thus, when FXR is activated by bile acids or bile acid derivatives, expression of guanylin or uroguanylin is upregulated, which then activates the GUCY2C signaling pathway. The addition of FXR agonistic ligands to the inventive pharmaceutical composition comprising a GUCY2C agonist, such as linaclotide, and a short chain C2 to C5 fatty acid and/or salt and/or prodrug thereof, such as butyrate or tributyrin, is regarded to increase the inventive synergistic effects.

According to the present invention, the one or more pharmaceutically acceptable excipients are generally chosen from suitable excipients for respective formulations, such as oral or rectal administrations. Such excipients for oral formulations, preferably tablets and granulates, may in particular be selected from the group consisting of binders, bulking agents/diluents/fillers, disintegrants, lubricants, glidants, adsorbents, sweeteners, flavorants, colourants, surfactants, polymers for modified release of the combination of GUCY2C and/or SCFA and polymers for protection of GUCY2C and/or SCFA. For rectal formulations (e.g., suppository, rectal gel or rectal foam), such excipients may in particular be selected from the group consisting of solvents, matrix builders, emulsifiers, mucoadhesive polymers, and amphiphilic excipients.

According to an embodiment of the present invention, the inventive pharmaceutical composition generally exhibits a suitable formulation for administering the therapeutically effective amount of the combination of a GUCY2C agonist and the SCFA. In view of the mechanism of action for the GUCY2C agonists, the inventive administration route is preferably oral or rectal.

Accordingly, the inventive pharmaceutical composition may preferably be an oral formulation, more preferably selected from the group consisting of a tablet, capsule, powder, and granulate. In view of the peptic/peptic mimetic structure of the GUCY2C agonists the oral formulation may preferably be enteric coated.

Alternatively, the inventive pharmaceutical composition may preferably be a rectal formulation, preferably selected from the group consisting of a suppository, rectal gel or rectal foam.

The inventive pharmaceutical composition as set out hereinbefore is preferably for use in preventing and/or treating colorectal tumorigenesis and/or carcinogenesis and/or chronic intestinal inflammation and/or cystic fibrosis related gastrointestinal manifestations. According to further embodiments of the present invention, the inventive pharmaceutical composition is preferably used, wherein colorectal tumorigenesis and/or carcinogenesis is preferably selected from the group consisting of colorectal cancer (CRC) including early stages preceding CRC, such as crypt dysplasia, crypt hyperplasia, colorectal adenoma, colorectal adenomatous polyps, or colorectal carcinoma; or wherein chronic intestinal inflammation is preferably selected from inflammatory bowel diseases (IBD) including Crohn's disease, or ulcerative colitis; or wherein cystic fibrosis related gastrointestinal manifestations preferably includes intestinal mucus inspissation, intestinal dysmotility, or distal intestinal obstruction syndrome.

As set out hereinbefore, the second aspect of the present invention relates to a method of preventing and/or treating colorectal tumorigenesis and/or carcinogenesis and/or chronic intestinal inflammation and/or cystic fibrosis related gastrointestinal manifestations, characterized in that the method comprises administering to a patient, who has or is at risk to develop colorectal tumorigenesis and/or carcinogenesis and/or chronic intestinal inflammation and/or cystic fibrosis related gastrointestinal manifestations, a therapeutically effective amount of a combination of a GUCY2C agonist and a short-chain C2 to C5 fatty acid and/or a salt and/or a prodrug thereof.

According to a further embodiment of the present invention, the colorectal tumorigenesis and/or carcinogenesis is preferably selected from the group consisting of colorectal cancer (CRC) including early stages preceding CRC, such as crypt dysplasia, crypt hyperplasia, colorectal adenoma, colorectal adenomatous polyps, or colorectal carcinoma; or wherein chronic intestinal inflammation is preferably selected from inflammatory bowel diseases (IBD) including Crohn's disease, or ulcerative colitis; or wherein cystic fibrosis related gastrointestinal manifestations preferably includes intestinal mucus inspissation, intestinal dysmotility, or distal intestinal obstruction syndrome.

According to another embodiment of the present invention, the therapeutically effective amount of a combination of a GUCY2C agonist and a short-chain C2 to C5 fatty acid and/or a salt and/or a prodrug thereof is preferably the inventive pharmaceutical composition according to the first inventive aspect.

All features and embodiments disclosed with respect to the first aspect of the present invention are combinable alone or in (sub-)combination with the second aspect of the present invention including each of the preferred embodiments thereof, provided the resulting combination of features is reasonable to a person skilled in the art.

The present invention is described in the following on the basis of exemplary embodiments, which merely serve as examples and which shall not limit the scope of the present protective right.

EXAMPLES

Further characteristics and advantages of the present invention will ensue from the following description of example embodiments of the inventive aspects with reference to the accompanying drawings.

All of the features disclosed hereinafter with respect to the example embodiments and/or the accompanying figures can alone or in any sub-combination be combined with features of the aspects of the present invention including features of preferred embodiments thereof, provided the resulting feature combination is reasonable to a person skilled in the art.

Experiment 1: Mouse Trial Using an AOM/DSS-Based CRC Mouse Model.

Thirty wild type mice (BALB/c) were maintained in individually ventilated cages (specific pathogen-free conditions) and divided in four age- and gender-matching groups at the age of 4 weeks. The schematic study set up of the mouse trial using AOM/DSS-based CRC mouse model is represented in FIG. 1.

Accordingly, group A received a semi-synthetic control diet (Hoevenaars F P M, van Schothorst E M, Horakova O, Voigt A, Rossmeisl M, Pico C, Caimari A, Kopecky J, Klaus S, Keijer J. BIOCLAIMS standard diet (BIOsd): a reference diet for nutritional physiology. Genes Nutr. 2012; 7:399-404), group B received a semi-synthetic diet with fiber-supplementation (containing about 46,2 g resistant starch type 2 per 1 kg diet), group C received a semi-synthetic control diet with linaclotide supplementation in drinking water (0.069 μg/mL; replaced every second day; dosage of linaclotide was calculated based on a previous study that applied 0.207 μg/day/mouse via oral gavage (Sharman S K, Islam B N, Hou Y, Singh N, Berger F G, Sridhar S, Yoo W, Browning D D. Cyclic-GMP-Elevating Agents Suppress Polyposis in ApcMin Mice by Targeting the Preneoplastic Epithelium. Cancer Prev Res (Phila Pa). 2018; 11:81-92.) and an assumed daily intake of 3 mL $H_2O$ per mouse; this mimics a daily intake of about 0.6 mg in a 70 kg healthy human, which is close to amounts used in previous clinical studies (Weinberg D S, Lin J E, Foster N R, Della'Zanna G, Umar A, Seisler D, Kraft W K, Kastenberg D M, Katz L C, Limburg P J, et al. Bioactivity of Oral Linaclotide in Human Colorectum for Cancer Chemoprevention. Cancer Prev Res Phila Pa. 2017; 10:345-54.)), group D received a combination of fiber-supplemented diet (containing about 46,2 g resistant starch type 2 per 1 kg diet), and linaclotide (0.069 μg/mL).

At the age of 8 weeks all mice received 3 injections (i.p.) of azoxymethane (AOM) (1 injection/week at a final concentration of 10 mg/kg body weight), which has carcinogenic properties and induces tumorigenesis in the colon of mice. Five days after the last injection of AOM all mice received 3 cycles of dextran sodium sulfate (DSS) added to the drinking water (1.5% DSS in drinking water for 5 days followed by 14 days without DSS) to induce a colitis. The chemical induction of colonic tumors in mice by treatment with AOM/DSS is used as a standard model to investigate pathogenesis of CRC and reflects the effects of pro-inflammatory processes contributing to tumorigenesis in the colon.

At the end of the treatment, mice were sacrificed and tissue samples taken for further analysis of colorectal tumorigenesis, inflammation and CRC-associated markers. A histological scoring with regard to intestinal inflammation (score: 0 as "no inflammation and no ulcers present" to 6 "severe inflammation and ulcers present") and tumorigenesis (score: 0 as "no hyperplasia or dysplasia" to 3 "tumors") of fixed and HE-stained whole colon sections was performed by a veterinarian in a blinded manner. Cecal SCFA were analyzed by gas chromatography.

Experiment 2: Organoids

Organoids were generated from mouse small intestine and colon using a standard protocol (VanDussen K L, Marinshaw J M, Shaikh N, Miyoshi H, Moon C, Tarr P I, Ciorba M A, Stappenbeck T S. Development of an enhanced human gastrointestinal epithelial culture system to facilitate patient-based assays. Gut. 2015; 64:911-20.). Organoids resemble "mini-guts" made from intestinal epithelial cells that are cultured in vitro and show a more physiological phenotype compared to human cancer cell lines. This is important in the context of prevention of CRC, since only "normal colonocytes" express physiological levels of guanylin and reveal physiological responses to butyrate. Organoids were cultured with different concentrations of sodium butyrate, linaclotide or both for 24 hours and bright-field pictures taken. In addition, formalin-fixed organoids were investigated for guanylin production using immunofluorescence staining and confocal laser microscopy following standard protocols.

Results and Discussion

Figure 2A:
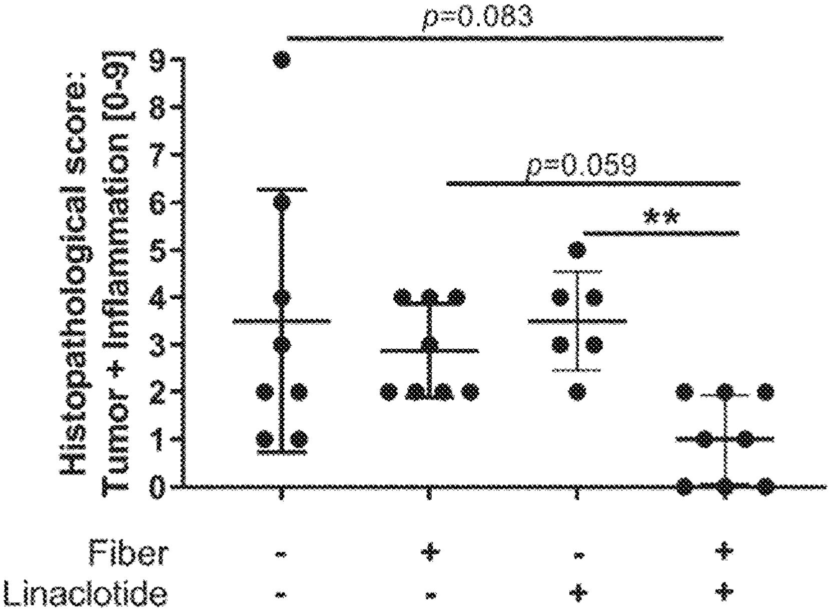
FIGS. 2 a) to d) represent graphs displaying a histopathological scoring of HE-stained whole colon sections of mice receiving a semi-synthetic control diet, fiber-supplemented diet, linaclotide or both and their respective effect on prevention of chronic intestinal inflammation and colonic tumor formation.
Figure 2B:
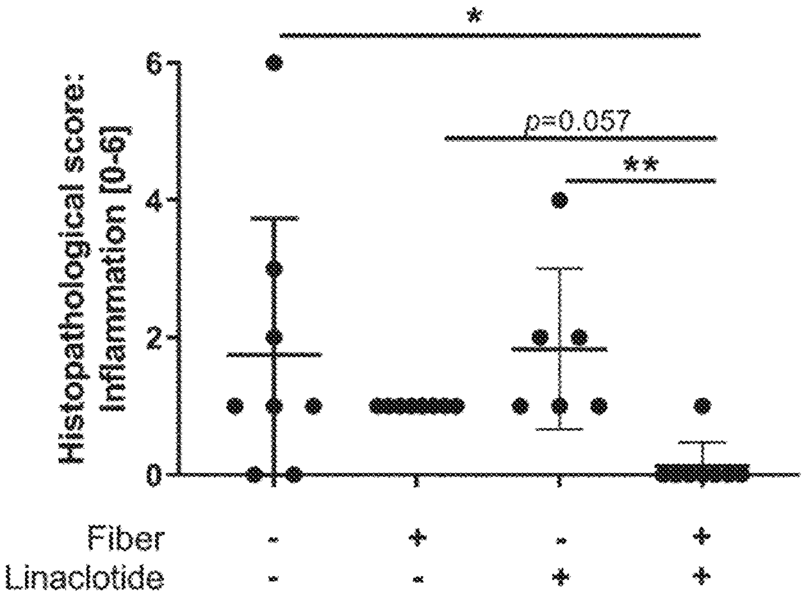
Figure 2C:
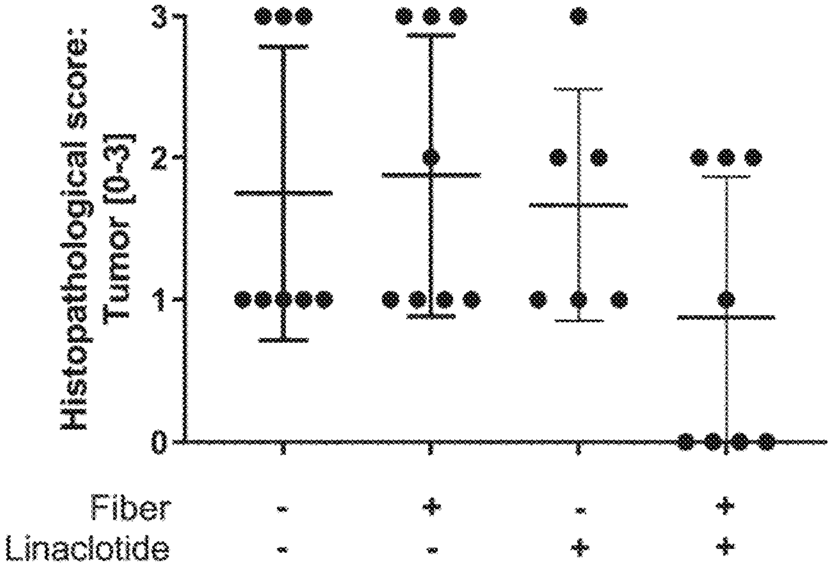
Figure 2D:
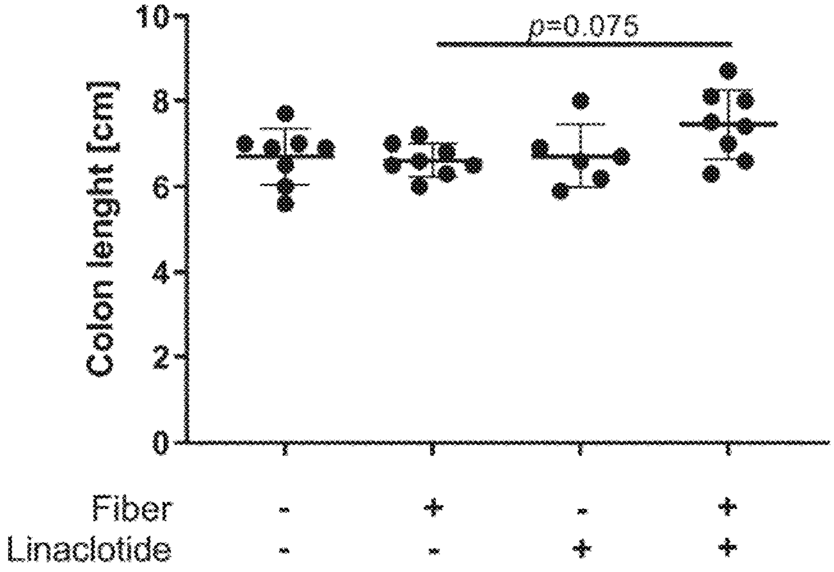

1. Synergistic Effects of Butyrate and GUCY2C Agonists that Prevent Chronic Intestinal Inflammation and Tumorigenesis in the Colon FIGS. 2 a) to c) represent graphs displaying a histopathological scoring of HE-stained whole colon sections of mice receiving a semi-synthetic control diet, fiber-supplemented diet, linaclotide or both and their respective effect on prevention of chronic intestinal inflammation and colonic tumor formation. FIG. 2*a*) shows combined, FIG. 2*b*) inflammation and FIG. 2*c*) tumor formation scores (0=no tumor/inflammation). FIG. 2*d*) shows colon length of mice receiving the different treatments. Single dots represent single mice; statistical analysis using One-way ANOVA with Kruskal-Wallis post-test with *=$p<0.05$, **=$p<0.01$.

Previous studies demonstrated tumorsuppressive activity of either butyrate or GUCY2C agonists, but did not investigate the effects of a combined administration.

Here, it is shown for the first time that butyrate (provided by fiber-supplemented diet) and linaclotide as a GUCY2C agonist have synergistic effects in prevention of experimental colonic inflammation and tumorigenesis compared with the single administration groups in a CRC mouse model (FIG. 2*a*). This synergistic effect was observed in inflammation—as well as tumor-related histopathological scorings of the whole mouse colon (FIG. 2*b,c*) and confirmed by colon length as macroscopic marker associated with inflammation (FIG. 2*d*) (colon is usually shorter in DSS-mediated severe inflammation). Although not always statistically significant, the overall pattern of the different treatment groups is consistent throughout the whole study and supports synergistic effects of butyrate and linaclotide as exemplified by the following analyses.

2. Stimulated GUCY2C Signaling Diminishes Fecal Butyrate Levels, Suggesting Enhanced Butyrate Absorption from Fiber-Supplemented Diet FIGS. 3 a) to d) represent graphs on the effect of linaclotide on diminishing SCFA in the cecal content under high-fiber conditions. The figures show quantification data of butyric acid (FIG. 3*a*), acetic acid (FIG. 3*b*), propionic acid (FIG. 3*c*) and valeric acid (FIG. 3*d*) in the cecal content of mice receiving a semi-synthetic control diet, fiber-supplemented diet, linaclotide or both. Single dots represent single mice; statistical analysis using One-way ANOVA with Kruskal-Wallis or Tukey post-test with *=$p<0.05$, **=$p<0.01$.

Figure 3A:
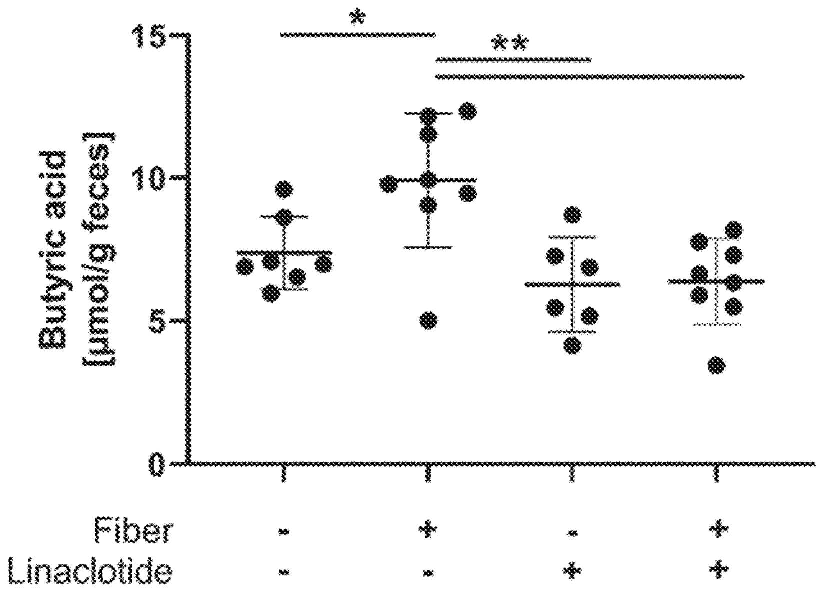
FIGS. 3 a) to d) represent graphs on the effect of linaclotide on diminishing SCFA levels in feces under high-fiber conditions.
Figure 3B:
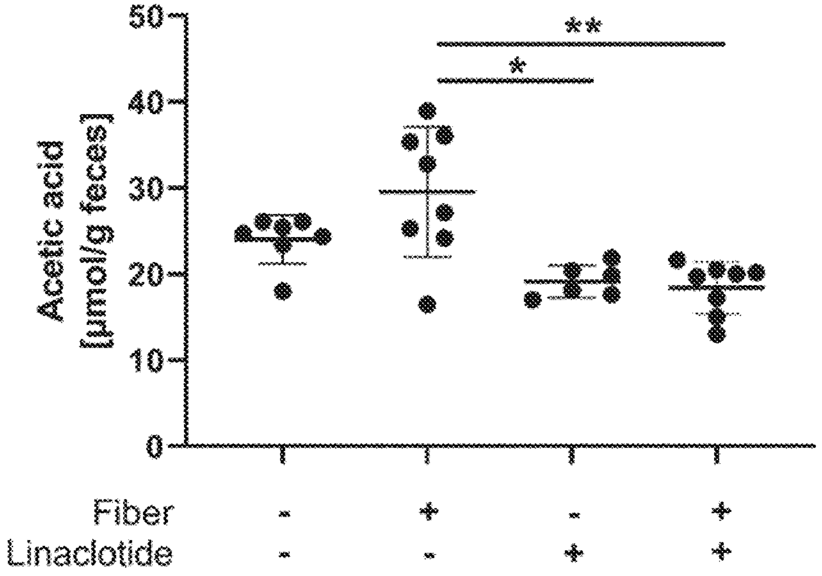
Figure 3C:
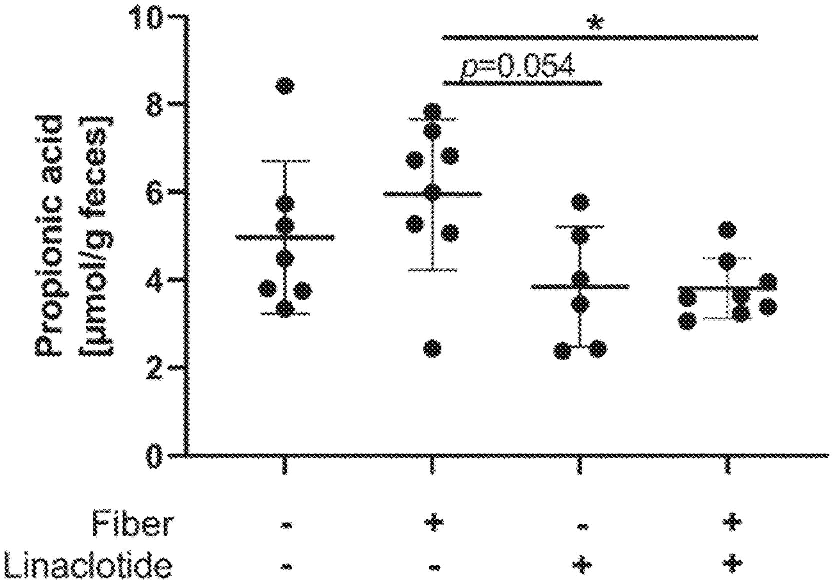
Figure 3D:
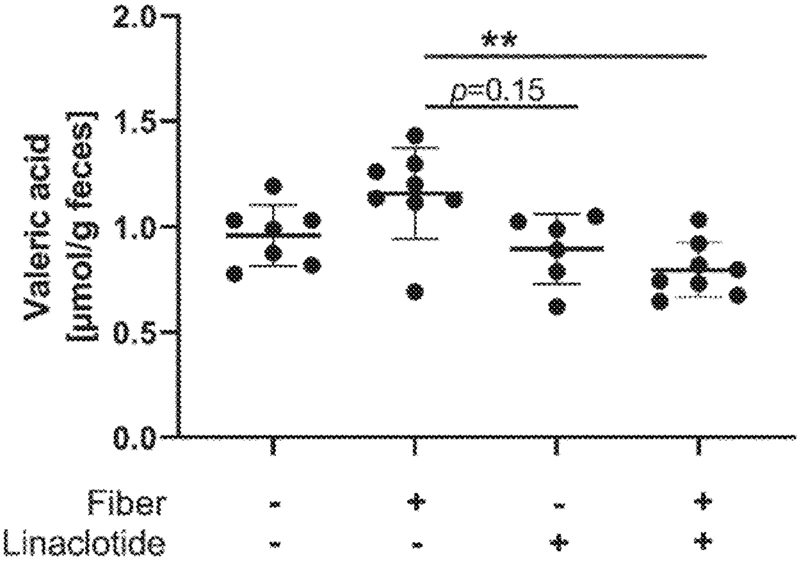

As expected, fiber-supplementation promoted significantly higher concentrations of butyrate in the cecal lumen compared to the control diet or linaclotide group (FIG. 3*a*). Consistent with previous studies, fiber supplementation also led to higher levels of other SCFA such as acetate and propionate (FIGS. 3*b-d*). There were no significant changes in cecal SCFA levels detected when linaclotide was administered alone. Interestingly, the combined treatment (fiber-supplemented diet and linaclotide) did not reproduce the high cecal butyrate levels found in the fiber-diet group, but resulted in a significantly lower butyrate concentration (FIG. 3*a*). This was completely unexpected and no studies seem to have been published that show similar effects of any agent on luminal butyrate levels, in particular for high-fiber diets. It suggests that the high cecal levels of butyrate, provided by fiber-supplemented diet, are completely abolished by linaclotide, reaching levels similar to the control diet or linaclotide group (FIG. 3*a*). This also applies for other fecal SCFA, suggesting that there may be (a) no increased production of SCFA, which seems to be unlikely given the results for the fiber-supplementation group or (b) an enhanced absorption of SCFA facilitated by linaclotide or GUCY2C signaling, respectively. Since most epithelial SCFA transporters are not specific for butyrate, GUCY2C signaling may stimulate their expression/presence boosting the uptake of butyrate and other SCFA, such as acetate, propionate or valerate.

3. Butyrate Limits the Osmotic Flow of $H_2O$ to the Intestinal Lumen Caused by GUCY2C Signaling.

Figure 4A:
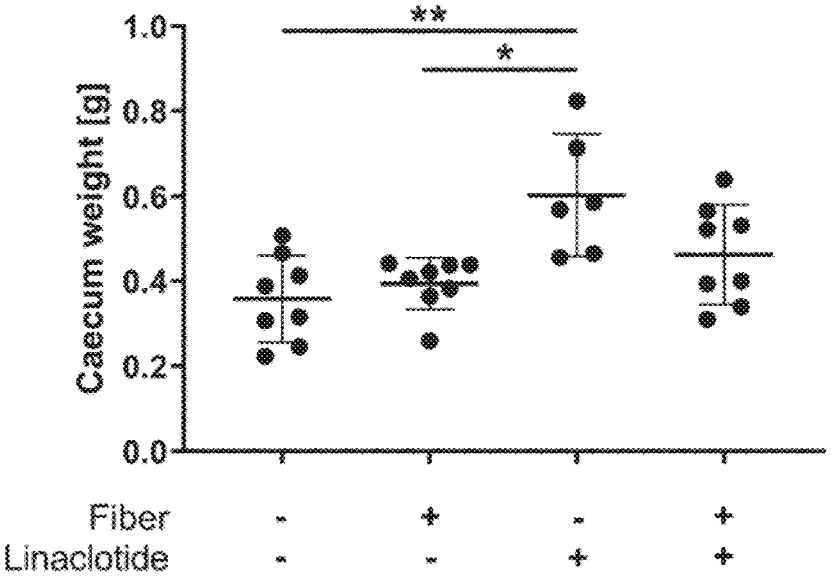
FIGS. 4 a) and b) represent graphs on the effect of butyrate on acting as osmotic antagonist of linaclotide and GUVY2C signaling limiting the flow of $H_2O$ to the gut lumen.
Figure 4B:
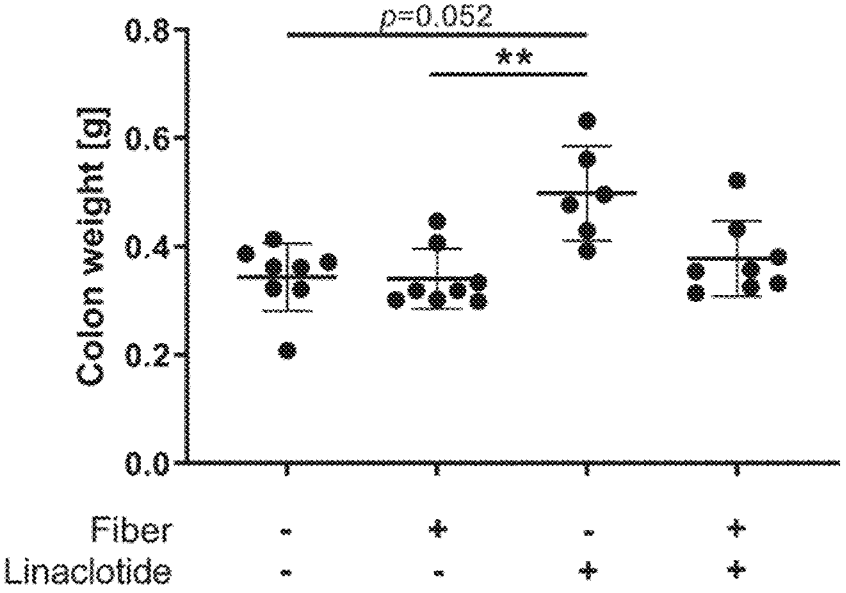
Figure 5A:
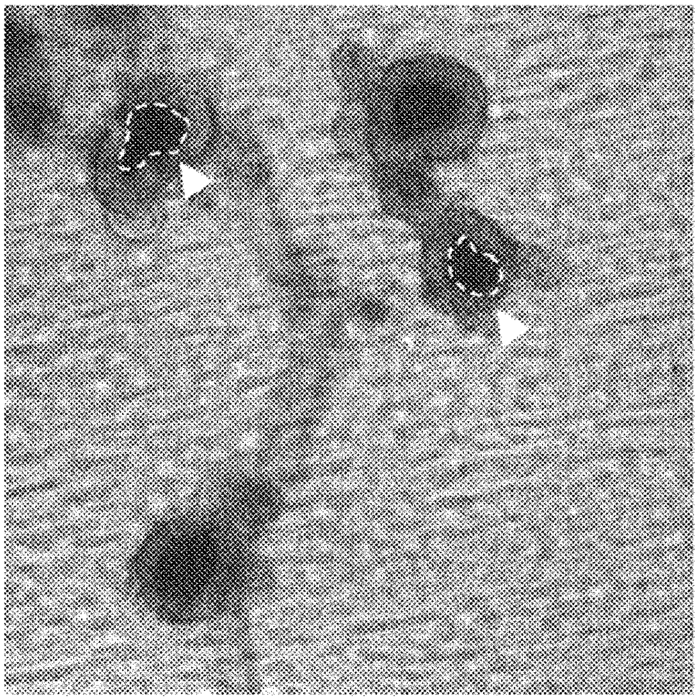
FIGS. 5 a) to d) represent bright-field images showing expansion of the lumen (white dashed lines) in mouse intestinal organoids (=in vitro "mini-guts", white arrows) cultured with PBS as untreated control (FIG. 5*a*), with sodium butyrate (FIG. 5*b*), linaclotide (FIG. 5*c*) or both (FIG. 5*d*) for 20 hours.
Figure 5B:
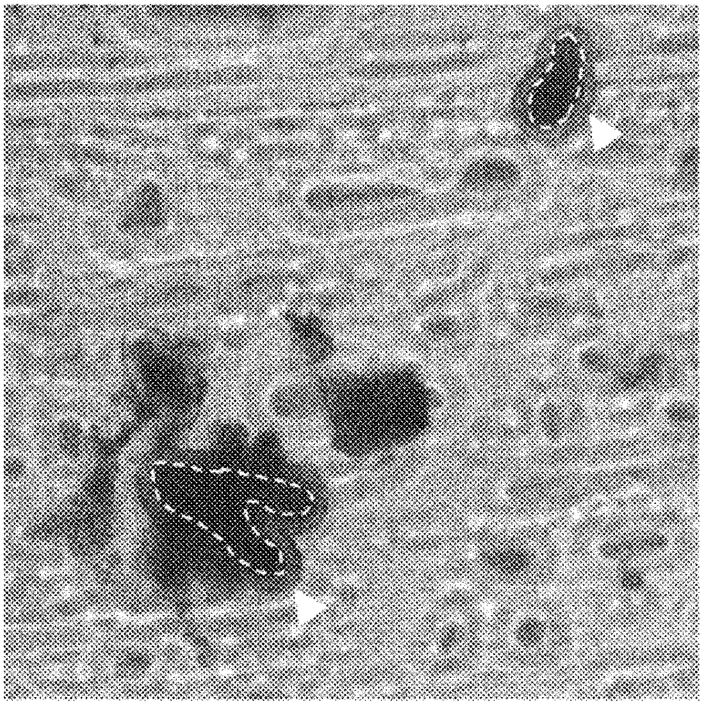
Figure 5C:
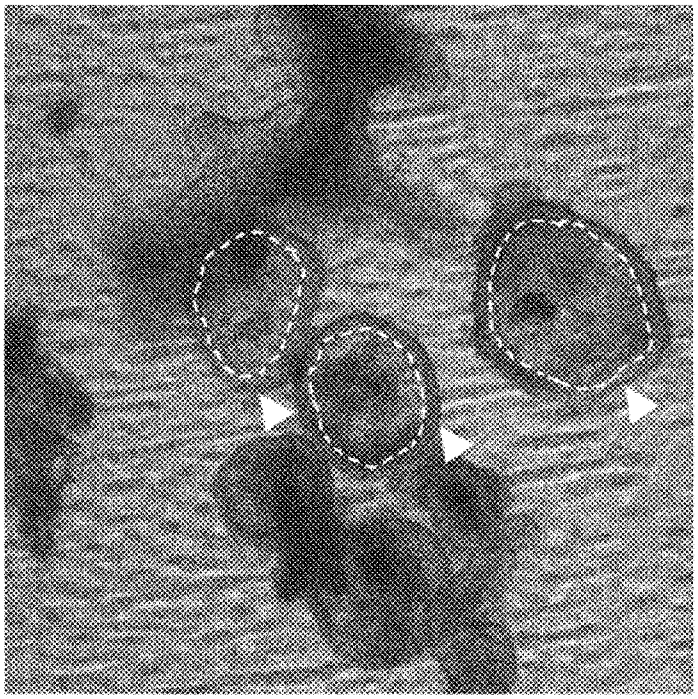
Figure 5D:
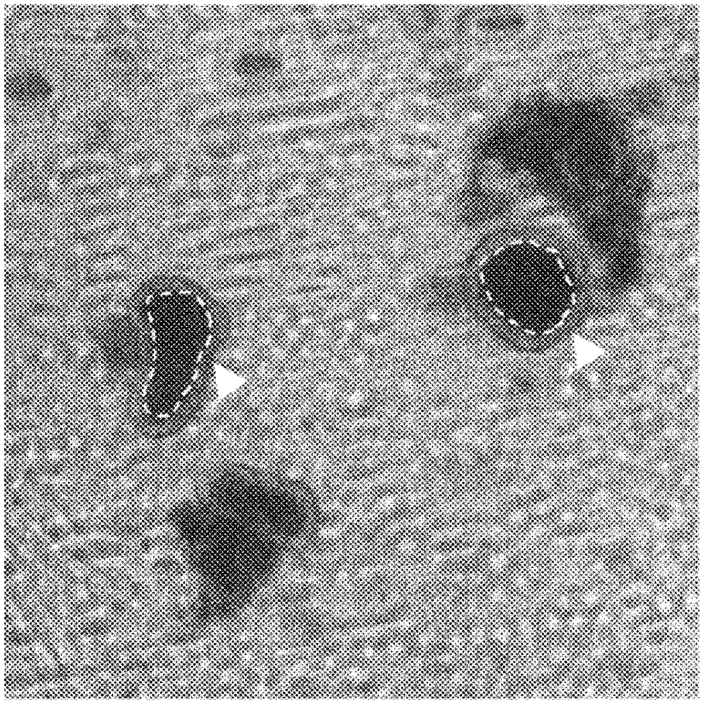

FIGS. 4 a) to d) represent graphs on the effect of butyrate acting as osmotic antagonist of linaclotide or GUCY2C signaling limiting the flow of $H_2O$ to the gut lumen. FIG. 4*a*) shows caecum and FIG. 4*b*) colon weight of mice receiving a semi-synthetic control diet, fiber-supplemented diet, linaclotide or both. Single dots represent single mice; statistical analysis using One-way ANOVA with Kruskal-Wallis post-test, *=$p<0.05$. **=$p<0.01$.

FIGS. 5 a) to d) show four representative bright-field images showing expansion of the lumen (white dashed lines) in mouse intestinal organoids (=in vitro "mini-guts", white arrows) cultured with sodium butyrate (2 mM), linaclotide (10 μM) or both for 20 hours, treatment with PBS represents the untreated control.

Figure 6A:
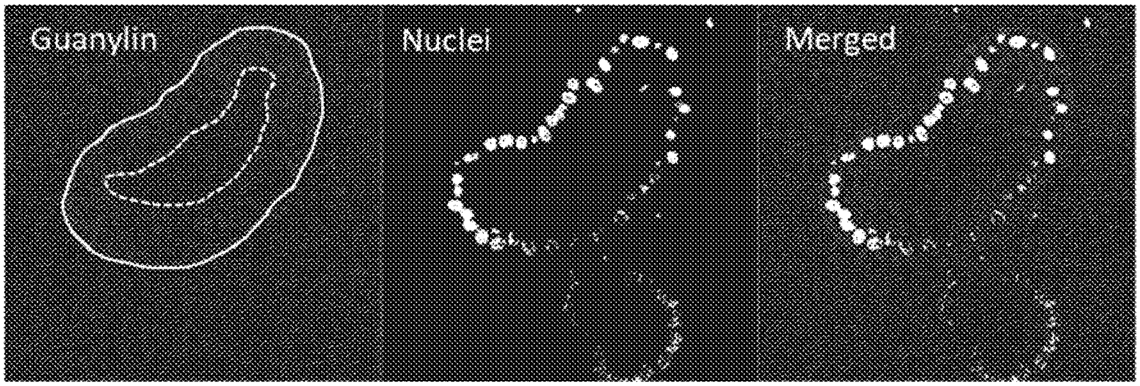
FIGS. 6*a*) to c) represent immunofluorescence staining images showing guanylin presence in the intestinal epithelium (area between solid and dashed white lines) of mouse intestinal organoids cultured with sodium butyrate (FIG. 6*a*), linaclotide (FIG. 6*b*) or both (FIG. 6*c*) for 20 hours, (left column=guanylin, middle column=cell nuclei, right column=merged images).

FIGS. 6*a*) to c) show three representative immunofluorescence staining images showing guanylin presence in the intestinal epithelium (area between solid and dashed white lines) of mouse intestinal organoids cultured with sodium butyrate (2 mM), linaclotide (10 μM) or both for 20 hours. (left column=guanylin, middle column=cell nuclei, right column=merged images).

Previous studies demonstrated that butyrate promotes an osmotic gradient of $H_2O$ towards the intestinal tissue, resulting in lower levels of $H_2O$ in the gut lumen. Similarly, studies showed that GUCY2C signaling supports a reciprocal osmotic flow towards the intestinal lumen, resulting in high levels of $H_2O$ in the gut lumen, which may cause diarrhea. However, a potential link between butyrate and GUCY2C signaling regarding osmotic counter-regulation was neither investigated nor suggested, yet.

As expected, mice receiving linaclotide had higher caecum and colon weights (indication of high amounts of $H_2O$ in the gut lumen) (FIGS. 4a,b). Of note, we did not observe the side effect diarrhea in these mice at the administered linaclotide concentration, which is consistent with previous data. For the combined treatment group, the mouse caecum and colon weights were similar to levels observed in the control or fiber group, suggesting lower amounts of $H_2O$ in the gut lumen and the limitation of the osmotic effects by high levels of butyrate (FIGS. 4a,b). This data shows, that the combined administration of GUCY2C, e.g. linaclotide, and a SCFA, e.g. butyrate or tributyrin, reduces the risk for the side effect diarrhea and serious dehydration following GUCY2C stimulation, e.g. by linaclotide administration.

The counter-regulating effect of butyrate on linaclotide-mediated osmotic gradients was also confirmed in an intestinal organoid culture, where the combination of butyrate and linaclotide led to a smaller 'organoid lumen' compared to linaclotide alone (FIGS. 5a to d).

Summary

What is the underlying mechanism of the observed synergistic effects of butyrate and the GUCY2C agonist linaclotide?

Figure 6B:
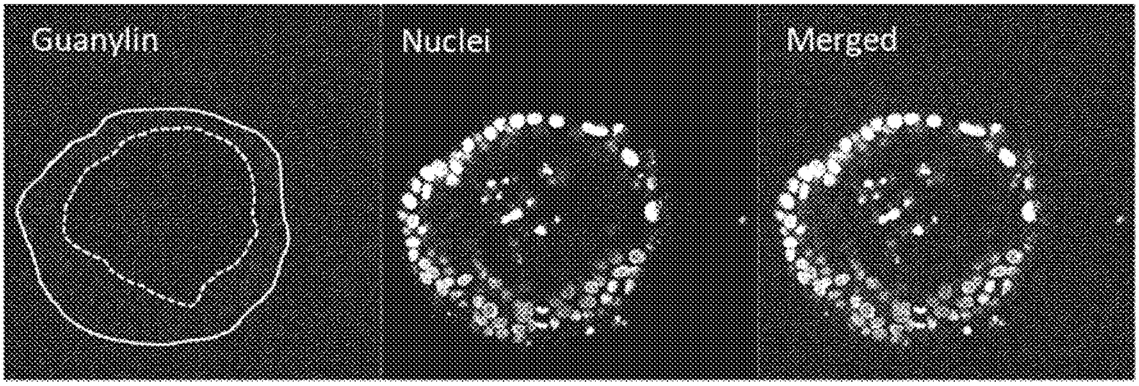
Figure 6C:
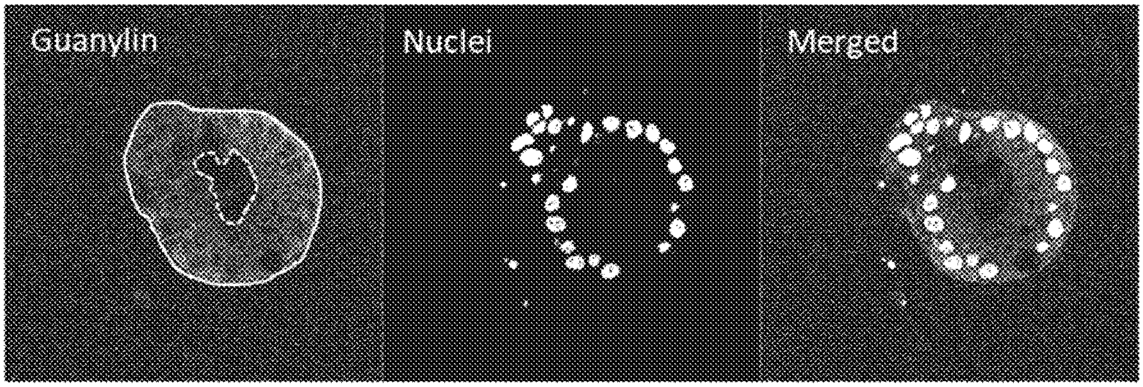

The above presented data shows that a combination of butyrate and linaclotide leads to an enhanced production of guanylin in intestinal epithelial cells, which seems to trigger GUCY2C signaling (FIGS. 6a to c) and, thus, facilitates the synergistic effect on preventing and/or treating colorectal tumorigenesis, preferably colorectal cancer (CRC), or chronic intestinal inflammation, preferably inflammatory bowel diseases (IBD).

The above presented data also points to a significantly improved osmotic balance at the intestinal epithelium facilitated by the osmotic antagonists butyrate and linaclotide (FIGS. 5a to d). This may promote the absorption of butyrate by intestinal epithelial cells and promote GUCY2C signaling. Accordingly, the inventive combined administration of a GUCY2C agonist, e.g. linaclotide, and a SCFA, e.g. butyrate and/or tributyrin, reduces the risk for the side effect diarrhea and serious dehydration following GUCY2C stimulation, e.g. by linaclotide administration.

The invention claimed is:

1. A pharmaceutical composition comprising a combination of a guanylate cyclase C (GUCY2C) agonist and a short-chain fatty acid and/or a salt and/or a prodrug thereof in a therapeutically effective amount and one or more pharmaceutically acceptable excipients, wherein the short-chain fatty acid is selected from the group consisting of butyric acid or a salt or ester thereof.

2. The pharmaceutical composition according to claim 1, wherein the short-chain fatty acid comprises sodium butyrate or tributyrin.

3. The pharmaceutical composition according to claim 1, wherein the composition comprises one or more GUCY2C agonists, which is/are selected from the group consisting of linaclotide, plecanatide, dolcanatide and STa toxin.

4. The pharmaceutical composition according to claim 1, wherein the pharmaceutical composition further comprises one or more farnesoid X receptor (FXR) agonists, one or more bile acids and/or one or more bile acid derivatives.

5. The pharmaceutical composition according to claim 4, wherein the composition wherein the one or more farnesoid X receptor (FXR) agonists are selected from the group consisting of chenodeoxycholic acid (IUPAC: (R)-((3R,5S,7R,8R,9S,10S,13R,14S,17R)-3,7-dihydroxy-10,13-dimethylhexadecahydro-1H-cyclopenta[α]phenanthren-17-yl)pentanoic acid), cholic acid (IUPAC: R)-4-((3R,5S,7R,8R,9S,10S,12S,13R,14S,17R)-3,7,12-Trihydroxy-10,13-dimethylhexadecahydro-1H-cyclopenta[α]phenanthren-17-yl)pentanoic acid), deoxycholic acid (IUPAC: (3α,5β,12α,20R)-3,12-Dihydroxycholan-24-oic acid), lithocholic acid (IUPAC: (4R)-4-[(3R,5R,8R,9S, OS,13R,14S,17R)-3-Hydroxy-10,13-dimethyl-2,3,4,5,6,7,8,9,11,12,14,15,16,17-tetradecahydro-11-cyclopenta[α]phenanthren-17-yl]pentanoic acid), taurocholic acid (IUPAC: 2-{[(3α,5μ,7α,12α)-3,7,12-trihydroxy-24-oxocholan-24-yl]amino}ethanesulfonic acid), ursodeoxycholic acid (IUPAC: (R)-4-((3R,5S,7S,8R,9S,10S,13R,14S,17R)-3,7-dihydroxy-10,13-dimethylhexadecahydro-1H-cyclopenta[α]phenanthren-17-yl)pentanoic acid), semi-synthetic obeticholic acid (IUPAC: 6α-ethyl-chenodeoxycholic acid), AND synthetic GW 4064 (IUPAC: 3-[2-[2-Chloro-4-[[3(2,6-dichlorophenyl)-5-(1-methylethyl)-4-isoxazolyl]methoxy]phenyl]ethenyl]benzoic acid).

6. The pharmaceutical composition according to claim 1, wherein the pharmaceutical composition is an oral formulation.

7. The pharmaceutical composition according to claim 6, wherein the oral composition is an enteric-coated oral formulation, selected from the group consisting of a tablet, a capsule, a powder and a granulate.

8. The pharmaceutical composition according to claim 1, wherein the pharmaceutical composition is a rectal formulation.

9. The pharmaceutical composition according to claim 8, wherein the rectal formulation is selected from the group consisting of a suppository, a rectal gel and a rectal foam.

10. The pharmaceutical composition according to claim 1, wherein the composition comprises the GUCY2C agonist linaclotide in an amount of 0.1 to 1,000 mg per dose unit.

11. The pharmaceutical composition according to claim 1, wherein the composition comprises the short chain fatty acid or a salt or a prodrug thereof in an amount of 0.1 to 5,000 mg per dose unit.

12. The pharmaceutical composition according to claim 11, wherein the short chain fatty acid comprises butyrate or tributyrin.

13. A method of preventing and/or treating colorectal tumorigenesis and/or carcinogenesis and/or chronic intestinal inflammation and/or cystic fibrosis related gastrointestinal manifestations, which the method comprises administering to a patient, who has or is at risk to develop colorectal tumorigenesis and/or carcinogenesis and/or chronic intestinal inflammation and/or cystic fibrosis related gastrointestinal manifestations, a pharmaceutical composition according to claim 1.

14. The method according to claim 13, wherein the colorectal tumorigenesis and/or carcinogenesis is selected from the group consisting of colorectal cancer (CRC), early stage preceding CRC, as crypt dysplasia, crypt hyperplasia, colorectal adenoma, colorectal adenomatous polyps, and colorectal carcinoma; inflammatory bowel diseases (IBD), Crohn's disease, and ulcerative colitis; or wherein the cystic fibrosis related gastrointestinal manifestations is selected from the group consisting of intestinal mucus inspissation, intestinal dysmotility, and distal intestinal obstruction syndrome.

15. The method according to claim 13, wherein the composition comprises the GUCY2C agonist linaclotide in an amount of 0.1 to 1,000 mg per dose unit.

16. The method according to claim 13, wherein the composition comprises the short chain fatty acid or a salt or a prodrug thereof, preferably butyrate or tributyrin in an amount of 0.1 to 5,000 mg per dose unit.

* * * * *